(12) United States Patent
Wang et al.

(10) Patent No.: US 8,906,947 B2
(45) Date of Patent: Dec. 9, 2014

(54) METHOD FOR THE SEPARATION AND PURIFICATION OF EPOTHILONES

(75) Inventors: Jidong Wang, Taizhou (CN); Hui Zhang, Taizhou (CN); Haibin Wang, Taizhou (CN); Lingping Ying, Taizhou (CN); Sheng Wang, Taizhou (CN); Xufang Guan, Taizhou (CN); Hua Bai, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 526 days.

(21) Appl. No.: 12/865,581

(22) PCT Filed: Feb. 1, 2008

(86) PCT No.: PCT/CN2008/000265
§ 371 (c)(1),
(2), (4) Date: Jul. 30, 2010

(87) PCT Pub. No.: WO2009/100571
PCT Pub. Date: Aug. 20, 2009

(65) Prior Publication Data
US 2010/0311796 A1 Dec. 9, 2010

(51) Int. Cl.
*C07D 493/04* (2006.01)
*C07D 417/06* (2006.01)
*A61K 31/427* (2006.01)
*A61P 35/00* (2006.01)

(52) U.S. Cl.
CPC ............ *C07D 417/06* (2013.01); *C07D 493/04* (2013.01)
USPC ........................................................ 514/365

(58) Field of Classification Search
None
See application file for complete search history.

(56) References Cited

FOREIGN PATENT DOCUMENTS

| CN | 1291239 | 4/2001 |
|---|---|---|
| CN | 1369484 | 9/2002 |
| CN | 1479741 | 3/2004 |
| CN | 1535971 | 10/2004 |
| CN | 1705662 | 12/2005 |
| CN | 101104884 | 1/2008 |

OTHER PUBLICATIONS

LaserchromHPLC-date, http://wayback.archive.org/web/20070801000000*/http:/www.laserchrom.co.uk/LaserchromHPLC-HPLCSolventGuide.htm, 2007.*
LaserchromHPLC, http://www.laserchrom.co.uk/LaserchromHPLC-HPLCSolventGuide.htm, 2007.*
Gerth, Klaus et al., Epothilons A and B: Antifungal and Cytotoxic Compounds from Sorgangium cellulosum (Myxobacteria), The Journal of Antibiotics, Jun. 1996, vol. 49, No. 6, pp. 560-563.
International Search Report for corresponding PCT application No. PCT/CN2008/000265, date of mailing Nov. 13, 2008.

* cited by examiner

*Primary Examiner* — Sun Jae Yoo
(74) *Attorney, Agent, or Firm* — Myers Bigel Sibley & Sajovec, P.A.

(57) ABSTRACT

The invention discloses a method for the separation and purification of epothilones, especially discloses a method for the separation and purification of epothilones B and A using normal phase silica gel chromatography, which comprises loading the sample after dissolving the sample containing epothilones B and A with $C_1$-$C_7$ alkyl halide compounds or mixing the sample with silica gel, then gradient eluting silica gel column by an elution solvent of normal phase silica gel column, and finally obtaining products.

21 Claims, 3 Drawing Sheets

Fowl Chart of Separation and Purification of Epothilones B and A

METHOD FOR THE SEPARATION AND PURIFICATION OF EPOTHILONES

CROSS REFERENCE TO RELATED APPLICATION

This application is a 35 U.S.C. §371 national phase application of PCT Application No. PCT/CN2008/000265, filed on Feb. 1, 2008, the disclosures and contents of which are hereby incorporated by reference as if recited in full herein. The above-referenced PCT International Application was published in Chinese as International Publication No. WO 2009/100571 A1.

FIELD OF THE INVENTION

The invention relates to a method for separation and purification of epothilones. In particular, the invention relates to a method for separation and purification of epothilones B and A.

BACKGROUND OF THE INVENTION

Epothilone is a novel natural cytotoxic compound produced by myxobacteria as a new cytotoxic active component stabilizing microtubules (See Gerth, K, et. al., J. Antibiot. 49: 560-563 (1966)). It is biologically similar to paclitaxel which has significant antineoplastic activity on various solid tumors of human beings. That is, epothilone induces tubulin-polymers to form a super stable state one, inhibits mitosis, and thereby suppresses reproduction of tumor cells in a manner similar to paclitaxel.

Epothilones are superior to paclitaxel-based medicines in sources, synthesis methods, hydrophilicity, antineoplastic activity, antitumor spectrum and so on. In addition, epothilones, preferably epothilone A and most preferably epothilone B, have various advantages than current therapies, particularly the treatment using paclitaxel which has induced drug tolerance of tumors. Therefore, as a novel antitumor drug, epothilones are deemed as a promising candidate to replace paclitaxel with great market potential. The structures of epothilones B and A are shown below.

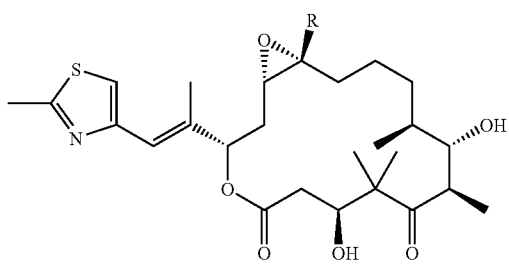

Epothilone A (R = H); Epothilone B (R = CH$_3$)

Since the antineoplastic activity of epothilones has been discovered in 1995, epothilones have been widely and deeply investigated from many aspects including chemistry, biology, medicine, pharmacy and so on, and certain results have been obtained.

With the advancement of research, there is an increasing need for epothilones with a high purity. Thus, how to separate and purify epothilones becomes an urgent problem to be solved. Many works have been made in China and oversea on epothilones, particularly processes for separation and purification of epothilones B and A. Chinese Patent No. ZL01820141.5, for example, discloses a method of separation and purification of epothilones, wherein desorption of epothilones, particularly epothilone A and/or epothilone B from a resin is disclosed. Chinese Patent No. ZL02110067.5 relates to a method of separation and purification of epothilones from fermentation broth of myxobacteria, wherein it discloses that technical means including adsorption by mixed resins, solid-liquid stepwise extraction, molecular sieve chromatography, crystallization and HPLC, etc are used to separate and obtain epothilones from fermentation broth of myxobacteria. In Chinese Patent No. ZL99803121.6, RP-HPLC is disclosed as a method used to purify epothilones B and A, while in patent No. CN03822662.6, normal HPLC is used to separate epothilones B and A.

Current techniques mainly use preparative chromatographic columns to separate and purify epothilones B and A, which not only need expensive apparatuses, but also consume a great amount of methanol or acetonitrile, with only a limited amount of product obtained in one time.

SUMMARY OF THE INVENTION

With respect to defects existing in the art of separation and purification of epothilone B and epothilone A, the object of the invention is to provide a novel method for separation and purification of epothilone B and epothilone A by using normal phase silica gel chromatography.

The method of the invention comprises:
dissolving a sample containing epothilones B and A in $C_1$-$C_7$ alkyl halide compound(s) to form a mixture, wherein the mixture is mixed with silica gel or not;
loading the mixture on a silica gel column;
gradient eluting the silica gel column with a normal phase silica gel column eluent;
collecting fractions; and
obtaining products.

Preferably, the method of the invention using normal phase silica gel chromatography for separation and purification of epothilone B and epothilone A further comprises the following steps:
dissolving a sample containing epothilones B and A in $C_1$-$C_7$ alkyl halide compound(s) to form a mixture, wherein the mixture is mixed with silica gel of a first normal phase silica gel column or not;
loading the mixture on the first normal phase silica gel column;
gradient eluting the silica gel column with a normal phase silica gel column eluent;
collecting fractions containing epothilone B and epothilone A;
combining the fractions containing epothilone B and epothilone A;
concentrating the combined fractions followed by crystallization to obtain a crude crystal containing epothilones B and A;
dissolving the crude crystal containing epothilones B and A in $C_1$-$C_7$ alkyl halide compound(s) to form a second mixture, wherein the second mixture is mixed with silica gel of a second normal phase silica gel column or not;
loading the second mixture on a second normal phase silica gel column;
gradient eluting the silica gel column with a normal phase silica gel column eluent;
collecting fractions containing epothilone B and fractions containing epothilone A respectively.

Epothilone B, after crystallization, is dissolved in t-butanol and lyophilized to obtain amorphous powder with a high purity; and epothilone A is dissolved in t-butanol and lyophilized to obtain amorphous powder with a high purity.

In the method of the invention using normal phase silica gel chromatography for separation of epothilones B and A, both of the first and second normal phase silica gel columns are those common in the art. In present invention, silica gel used in the first and second normal phase silica gel columns may be the same or different, and the same silica gel used for both columns is preferred.

In the method of the invention using normal phase silica gel chromatography for separation of epothilones B and A, the preferred amount of the silica gel used in the first normal phase silica gel column has a mass ratio of the silica gel to the sample of 5-10:1, and the amount of the silica gel used in the second normal phase silica gel column has a mass ratio of the silica gel to the crystal sample of 50-200:1.

The normal phase silica gel column is preferred to be balanced by a solvent of $C_1$-$C_7$ alkyl halide compound(s) before use so as to obtain better yields of epothilone B and epothilone A. Preferably, $C_1$-$C_7$ alkyl halide compound(s) may be one or more of dichloromethane, trichloromethane and bromoethane, wherein dichloromethane, trichloromethane or a combination thereof is more preferred.

The gradient eluent of the normal phase silica gel columns of the invention may be $C_1$-$C_7$ hydrocarbons, $C_1$-$C_7$ alkyl halide compound(s), $C_1$-$C_7$ ketones, $C_1$-$C_7$ esters or any combinations thereof, wherein $C_1$-$C_7$ hydrocarbons may be one or more selected from petroleum ether, n-hexane, cyclohexane and n-heptane, wherein petroleum ether is further preferred;

$C_1$-$C_7$ alkyl halide compound(s) may be one or more selected from dichloromethane, trichloromethane and bromoethane, wherein dichloromethane is further preferred;

$C_1$-$C_7$ ketones may be selected from acetone, butanone and a combination thereof; wherein acetone is further preferred;

$C_1$-$C_7$ esters may be selected from ethyl acetate, isobutyl acetate and a combination thereof; wherein ethyl acetate is further preferred.

The more preferred gradient eluent of the normal phase silica gel column of the invention may be one or a combination of two or more selected from petroleum ether, ethyl acetate, acetone, trichloromethane and dichloromethane.

Preferably, the eluent of the first normal phase silica gel column is a combination of acetone and petroleum ether, or a combination of ethyl acetate and petroleum ether. In the combination of acetone and petroleum ether, the preferred volume ratio of acetone and petroleum ether is 1:3-9, and in the combination of ethyl acetate and petroleum ether, the preferred volume ratio of ethyl acetate and petroleum ether is 1:1-9.

Preferably, the eluent of the second normal phase silica gel column is a combination of acetone and petroleum ether, or a combination of petroleum ether and acetone with either dichloromethane or trichloromethane. In the combination of acetone and petroleum ether, the volume ratio of acetone and petroleum ether is 1:3-9, and in the combination of petroleum ether and acetone with either dichloromethane or trichloromethane, the volume ratio of acetone and petroleum ether is 1:3-9, and the volume of dicholomethane or trichloromethane is 5%-50% of the total volume.

In the process of separation and purification of epothilone B and epothilone A by normal phase silica gel chromatography, crystallization of epothilones B and A may be performed by any conventional techniques in the art. In order to achieve better performance, it is preferred to use n-heptane, ethyl acetate, or a combination thereof as the solvent for crystallization. It is more preferred that crystallization solvent is a mixture of n-heptane and ethyl acetate with a volume ratio of 1:1. The crystallization may be preferably performed by solving the crude product containing epothilones B and A, or the crude product containing epothiloine B in an appropriate amount of ethyl acetate, adding n-heptane therein and letting the solution stand at room temperature, then cooling to 4° C. so as to obtain crystals.

In the process of separation and purification of epothilone B and epothilone A by normal phase silica gel chromatography, the sample containing epothilones B and A that is loaded on the first normal phase silica gel column is obtained by treating a fermentation broth of a strain of myxobacteria that generates epothilones with conventional means and then removing impurities therein.

In order to achieve the object of the invention better, the sample containing epothilones B and A that is loaded on the first normal phase silica gel column is a crude product obtained by treating a fermentation broth containing epothilones B and A with non-polar macroporous polymeric adsorbents. Specifically, the method is performed as:

adding a resin of a first non-polar macroporous polymeric adsorbent column into the fermentation broth of myxobacteria, and filtering by a vibrating screen and washing by water to remove impurities at the same time, and then loading the resin in a column, gradient eluting with an alcohol solution, and combining fractions containing epothilones B and A;

diluting the combined fractions containing epothilones B and A to an appropriate concentration, then loading the diluted solution on a second non-polar macroporous polymeric adsorbent column, gradient eluting with an alcohol solution, collecting fractions containing epothilones B and A, combining the fractions and then obtaining the sample containing epothilones B and A.

In present invention, the first non-polar macroporous resin and the second non-polar macroporous resin are non-polar macroporous polymeric adsorbents used to separate epothilones from the fermentation broth. The non-polar macroporous polymeric adsorbents may be the same or different.

The preferred first non-polar macroporous polymeric adsorbent of present invention may be XAD-1600 or HP-20, such as Amberlite XAD-1600 (Rohm & Haas, America) and Diaion HP-20 (Mitsubishi Chemical, Japan), wherein XAD-1600 is more preferred.

The preferred second non-polar macroporous polymeric adsorbent of present invention may be non-polar macroporous polymeric adsorbents of H41 or H60 (produced by Chinese Academy of Forestry Institute of Chemical Engineering, Nanjing Science and Technology Development Corporation), wherein non-polar macroporous polymeric adsorbents of H41 are more preferred.

The eluent used in the first non-polar macroporous polymeric adsorbent and the second non-polar macroporous polymeric adsorbent is an alcohol solution, such as a solution of ethanol or methanol. An ethanol solution is preferred. A more preferred eluent used for the first non-polar macroporous polymeric adsorbent is an ethanol solution of 30%-100% by volume; and an eluent used for the second non-polar macroporous polymeric adsorbent is an ethanol solution of 30%-80% by volume.

In the process of separation and purification of epothilone B and epothilone A by normal phase silica gel chromatography, the fractions eluted from the adsorbents and the fractions eluted from the normal phase silica gel columns are measured by HPLC, and the fractions preferred to be collected are those:

fractions from the first non-polar macroporous polymeric adsorbent have over 50 ferment units based on total of epothilones B and A by analysis of HPLC;

fractions from the second non-polar macroporous polymeric adsorbent have over 50 ferment units based on total of epothilones B and A by analysis of HPLC;

fractions from the first normal phase silica gel column have more than 80% chromatographic purity based on total of epothilones B and A by analysis of HPLC; and fractions from the second normal phase silica gel column have more than 97.5% chromatographic purity based on epothilone B and more than 92.5% chromatographic purity based on epothilone A by analysis of HPLC.

The analysis of HPLC may be performed by any conventional methods in the art, wherein the following process is preferred:

a reversed-phase semi-preparative column (Agilent ZORBAX Eclipse XDB-C18), 250*9.4 mm, 5 μm of particle diameter of fillers, 1.5 mL/min of flow rate, measured at 249 nm, and methanol:water=80:20 as mobile phase; or an analytical column (SHIMADZU XOD-C18), 150*6.0 mm, 5 μm of particle diameter of fillers, 1.0 mL/min of flow rate, measured at 249 nm, and acetonitrile:methanol:water=40:20:50 as mobile phase.

According to a preferred embodiment of the invention for separation and purification of epothilone B and epothilone A by normal phase silica gel chromatography, the method comprises the following steps:

(1) filtering the fermentation broth wherein XAD-1600 type resin is added by a vibrating screen and washing by water to remove impurities at the same time, then loading the resin in a column, gradient eluting with an ethanol solution of 30%-100% by volume, collecting fractions sectionally, collecting respectively fractions containing epothilone B and epothilone A after analysis by HPLC, and then combining fractions containing epothilone B and epothilone A;

(2) diluting the combined fractions containing epothilones B and A to form an alcohol solution with an appropriate concentration, or concentrating combined fractions to a suitable volume by vacuum evaporation and then diluting to form an alcohol solution with an appropriate concentration, loading the alcohol solution on H41 type resin column, and gradient eluting with an alcohol solution of 30%-80% by volume, collecting fractions sectionally, collecting fractions containing epothilone B and epothilone A after analysis by HPLC, combining fractions containing epothilone B and epothilone A, concentrating the combined fractions by vacuum evaporation until dry so as to obtain a sample containing epothilones B and A;

(3) dissolving the sample containing epothilones B and A in trichloromethane or dichloromethane, wherein the mixture is mixed with silica gel of a first normal phase silica gel column or not; then loading the mixture on the first normal silica gel column, gradient eluting by a mixture of petroleum ether/acetone or a mixture of petroleum ether/ethyl acetate, collecting fractions sectionally, collecting fractions containing epothilone B and epothilone A after analysis by HPLC, combining fractions containing epothilone B and epothilone A, concentrating combined fractions by vacuum evaporation until dry, performing crystallization by a mixed solvent of ethyl acetate/n-heptane to obtain crude crystal containing epothilones B and A;

(4) dissolving the crude crystal containing epothilones B and A in trichloromethane or dichloromethane, wherein the second mixture is mixed with silica gel of a second normal phase silica gel column or not; then loading the second mixture on the second normal silica gel column, gradient eluting by a mixture of petroleum ether/acetone or a mixture of petroleum ether/acetone/trichloromethane, collecting fractions sectionally, collecting respectively fractions containing epothilone B and fractions containing epothilone A after analysis by HPLC;

(5) performing crystallization on fractions containing epothilone B by ethyl acetate/n-heptane, then dissolving the crystal in t-butanol and lyophilizing the solution to obtain product in a form of amorphous power with a high purity; dissolving epothilone A in t-butanol and lyophilizing the solution to obtain a product in a form of amorphous power with a high purity.

According to actual requirement on purity, epothilone B or epothilone A obtained from step (5) may be further purified. For example, epothilone B may be further purified by re-crystallization as described in the invention, and epothilone A may be purified by the second normal phase silica gel column of the invention again, so that epothilone B or epothilone A with a higher purity, such as 99.0% or above, may be obtained.

Epothilone B: ESIMS m/z 508 [M+H]$^+$; $^1$H NMR (CDCl$_3$, 400 MHz) δ: 6.98 (1H, s, H-19), 6.60 (1H, bs, H-17), 5.42 (1H, dd, J=7.9, 2.8 Hz, H-15), 4.24 (1H, m, H-3), 3.77 (1H, dd, J=8.4, 4.2 Hz, H-7), 3.30 (1H, m, H-6), 2.82 (1H, dd, J=7.7, 4.5 Hz, H-13), 2.70 (3H, s, H-21), 2.54 (1H, dd, J=14.1, 10.6 Hz, H-2a), 2.38 (1H, dd, J=14.1, 3.0 Hz, H-2b), 2.10 (1H, m, H-14a), 2.09 (3H, d, J=1.0 Hz, H-27), 1.90 (1H, m, H-14b), 1.72 (2H, m, H-8, H-11a), 1.49 (2H, m, H-10), 1.41 (3H, m, H-9, and H-11b), 1.39 (3H, s, H-23), 1.28 (3H, s, H-26), 1.17 (3H, d, J=6.8 Hz, H-24), 1.08 (3H, s, H-22), 1.00 (3H, d, J=7.0 Hz, H-25); $^{13}$C NMR (CDCl$_3$, 100 MHz) δ 220.6 (s, C-5), 170.6 (s, C-1), 165.2 (s, C-20), 151.8 (s, C-18), 137.6 (s, C-16), 119.6 (d, C-17), 116.1 (d, C-19), 76.7 (d, C-15), 74.1 (d, C-7), 72.8 (d, C-3), 61.7 (d, C-12), 61.4 (s, C-13), 53.1 (s, C-4), 42.9 (d, C-6), 39.2 (t, C-2), 36.4 (d, C-8), 32.4 (t, C-11), 32.1 (t, C-14), 30.7 (t, C-9), 22.7 (q, C-26), 22.3 (t, C-10), 21.5 (q, C-23), 19.5 (q, C-22), 19.1 (q, C-21), 17.1 (q, C-25), 15.9 (q, C-27), 13.6 (q, C-24).

Epothilone A: ESIMS m/z 494 [M+H]$^+$; $^1$H NMR (CDCl$_3$, 400 MHz) δ 6.98 (1H, s, H-19), 6.60 (1H, bs, H-17), 5.44 (1H, dd, J=8.7, 2.1 Hz, H-15), 4.20 (1H, m, H-3), 4.10 (1H, br s, 3-OH), 3.79 (1H, dd, J=8.4, 4.2 Hz, H-7), 3.22 (1H, m, H-6), 3.04 (1H, m, H-13), 2.92 (1H, m, H-12), 2.70 (3H, s, H-21), 2.52 (1H, dd, J=14.5, 10.6 Hz, H-2a), 2.42 (1H, dd, J=14.5, 3.2 Hz, H-2b), 2.12 (1H, m, H-14a), 2.09 (3H, d, J=1.0 Hz, H-27), 1.88 (1H, m, H-14b), 1.75 (2H, m, H-8, H-11a), 1.56 (1H, m, H-10a), 1.44 (4H, m, H-9, H-10b and H-11b), 1.41 (3H, s, H-23), 1.17 (3H, d, J=6.8 Hz, H-24), 1.10 (3H, s, H-22), 1.00 (3H, d, J=7.0 Hz, H-25); $^{13}$C NMR (CDCl$_3$, 75 MHz) δ 220.1 (s, C-5), 170.6 (s, C-1), 165.1 (s, C-20), 151.8 (s, C-18), 137.5 (s, C-16), 119.8 (d, C-17), 116.2 (d, C-19), 76.5 (d, C-15), 74.5 (d, C-7), 73.0 (d, C-3), 57.5 (d, C-12), 54.7 (d, C-13), 53.0 (s, C-4), 43.3 (d, C-6), 39.0 (t, C-2), 36.2 (d, C-8), 31.5 (t, C-14), 30.5 (t, C-9), 27.2 (t, C-11), 23.4 (t, C-10), 21.7 (q, C-23), 20.1 (q, C-22), 19.1 (q, C-21), 17.1 (q, C-25), 15.8 (q, C-27), 14.1 (q, C-24).

According to present invention, a flow chart for illustration of separation and purification of epothilones B and A is shown in FIG. 1.

The method of the invention can well separate epothilone B from epothilone A to obtain epothilone B and epothilone A with a purity of over 95.0%, preferably over 99.0%. Furthermore, comparing with techniques for separation of epothilones B and A in the art, the method of the invention has many advantages such as higher yield, simpler process and better operability. The method of the invention needs no expensive apparatus for preparing chromatographic columns, and is more suitable for industrial production. In addition, the method of the invention doesn't consume a great amount of solvent having high toxicity, such as methanol and acetonitrile.

DETAILED DESCRIPTION OF THE INVENTION

Example 1

Figure 1:
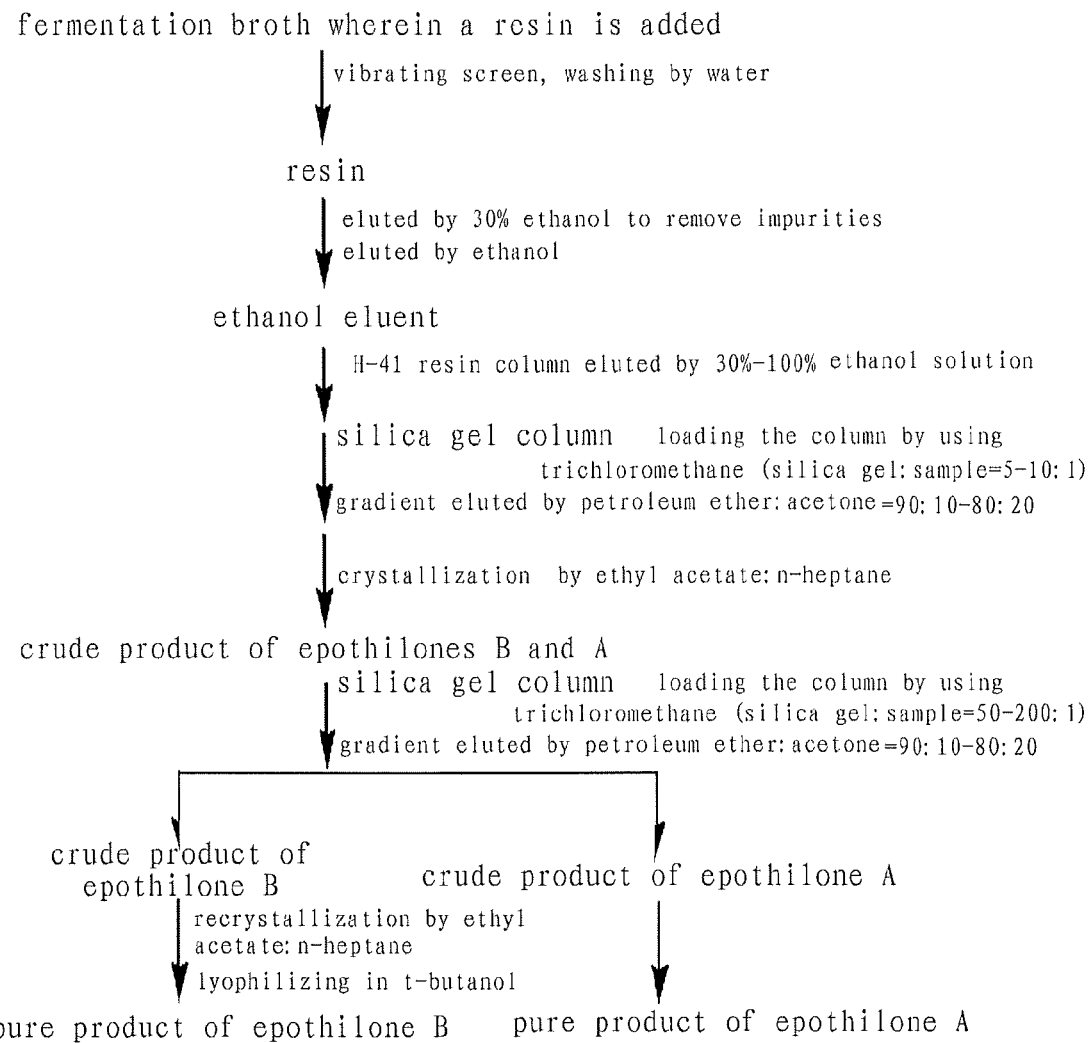
FIG. 1 is a flow chart for illustration of separation and purification of epothilone B and epothilone A.

3 ton fermentation broth of epothilones, wherein XAD-1600-type resin had been added, was filtered by a vibrating screen and washed by water. The resin was loaded in a column using a 30% ethanol solution, and then the column was eluted by an ethanol solution of 95%. Fractions were collected sectionally, and fractions containing epothilones B and A were collected and combined after analysis by HPLC. The combined fractions was condensed to 10 L, which contained 54.38 g epothilone B and 110.50 g epothilone A after analysis by HPLC (external standard method).

The obtained 10 L solution was prepared to be an ethanol solution of 30%. The ethanol solution was loaded on a H41-type resin column (20 cm*300 cm, bed volume: 70 L), and then the column was eluted with ethanol solutions of 30%, 40%, 50% and 60% in sequence with a two bed volume per concentration. The column was eluted by a 70% ethanol solution at last. Fractions were collected sectionally, and fractions containing epothilones B and A were collected and combined after analysis by HPLC. The combined fractions was condensed until dry so as to obtain a sample containing epothilones B and A.

The sample containing epothilones B and A was dissolved in $CHCl_3$. The dissolved sample was loaded on a first normal phase silica gel column (silica:sample=5:1), and then eluted by petroleum ether/ethyl acetate (80:20 by volume) for three bed volumes first, followed by petroleum ether/acetone (85:15 by volume) for two bed volumes and petroleum ether/acetone (80:20 by volume) for four bed volumes in sequence. Fractions were collected sectionally. Desired fractions containing epothilones B and A were collected after analysis by HPLC, combined, and then concentrated until dry.

The concentrated product was crystallized twice by using ethyl acetate/n-heptane of a ratio of 1:1 so as to obtain crude crystal containing epothilones B and A, which contains 40.26 g epothilone B and 31.81 g epothilone A measured by HPLC (external standard method) with a total chromatographic purity of 97.9%.

Example 2

After dissolving 5 g crude crystal containing epothilones B and A obtained from Example 1 in 5 ml dichloromethane, the solution was loaded on a second normal phase silica gel column (4 cm*80 cm, 300 g silica gel). The silica gel column was balanced by dichloromethane, and then gradient eluted in sequence with petroleum ether/acetone with ratios of 90:10, 85:15, 83:17 and 80:20. Fractions were collected sectionally. Desired fractions containing epothilone B and desired fractions containing epothilone A were collected and combined respectively after analysis by HPLC, and then condensed respectively until dry. Finally, 2.40 g epothilone B of 98.7% (yield 89%) and 1.90 g epothilone A of 95.8% (yield 92%) were obtained.

Example 3

After dissolving 5 g crude crystal containing epothilones B and A obtained from Example 1 in 5 ml trichloromethane, the solution was loaded on a second normal phase silica gel column (4 cm*80 cm, 300 g silica gel). The silica gel column was balanced by trichloromethane, and then gradient eluted in sequence with petroleum ether/acetone/trichloromethane with ratios of 90:10:10, 85:15:10, 83:17:10 and 80:20:10. Fractions were sectionally collected. Desired fractions containing epothilone B and desired fractions containing epothilone A were collected and combined respectively after analysis by HPLC, and then condensed respectively until dry. Finally, 2.48 g epothilone B of 98.9% (yield 92%) and 1.88 g epothilone A of 96.7% (yield 90%) were obtained.

Example 4

After dissolving 5 g crude crystal containing epothilones B and A obtained from Example 1 in 5 ml dichloromethane, the solution was loaded on a second normal phase silica gel column (6 cm*100 cm, 800 g silica gel). The silica gel column was balanced by dichloromethane, and then gradient eluted in sequence with petroleum ether/acetone/dichloromethane with the ratios of 90:10:40, 85:15:30, 83:17:20 and 80:20:10. Fractions were sectionally collected. Desired fractions containing epothilone B and desired fractions containing epothilone A were collected and pooled respectively after analysis by HPLC, and then condensed respectively until dry. Finally, 2.53 g epothilone B of 98.5% (yield 94%) and 1.94 g epothilone A of 97.8% (yield 92%) were obtained.

Example 5

Epothilone B with a high purity was obtained by re-crystallization of epothilone B obtained from Example 2-4; and epothilone A with a high purity was obtained by purifying obtained epothilone A by silica gel again.

10 g epothilone B sample with a HPLC chromatographic purity of 98.5% was dissolved in 15 ml ethyl acetate by heating to 52° C., and then 15 ml n-heptane was added therein. The obtained solution stood at room temperature and then was cooled to 4° C. for 24 hours. The solution was filtered and above steps were repeated on obtained crystal. Finally, 8.7 g crystal pure epothilone B of 99.4% was obtained.

After dissolving 5 g epothilone A with a HPLC chromatographic purity of 97.5% obtained from Examples 2-4 in 5 ml dichloromethane, the solution was loaded on a second normal phase silica gel column (300 g silica gel). The silica gel column was balanced by dichloromethane, and then gradient eluted in sequence with petroleum ether/acetone/dichloromethane with ratios of 90:10:40, 85:15:30, 83:17:20 and 80:20:10. Fractions were collected sectionally. Desired fractions containing epothilone A were collected, combined after analysis by HPLC, and then condensed until dry. Finally, 4.3 g epothilone of A 99.5% was obtained.

Figure 2:
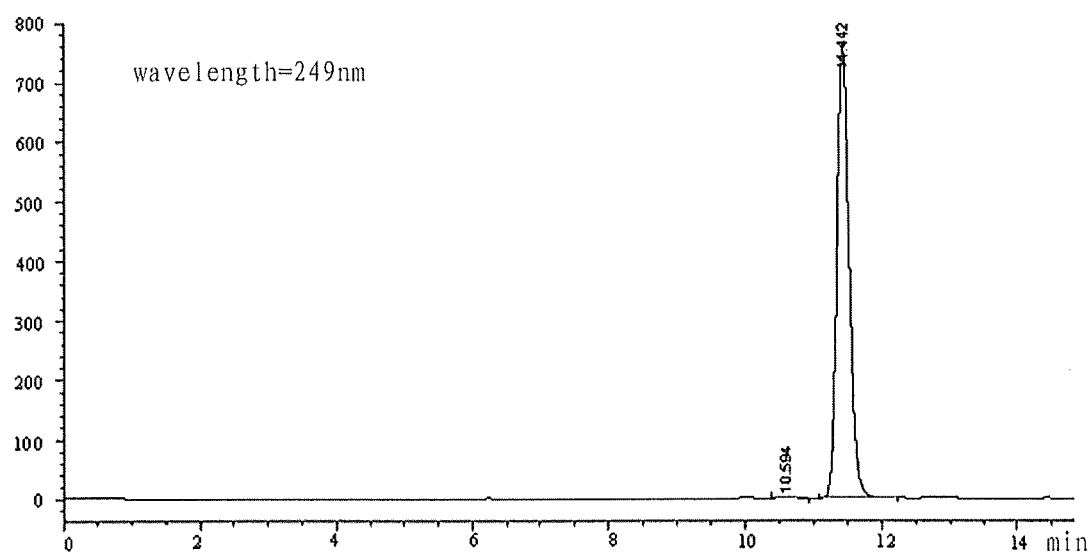
FIG. 2 is a HPLC chromatogram of epothilone B having a chromatographic purity of higher than 99.0% after the separation and purification.
Figure 3:
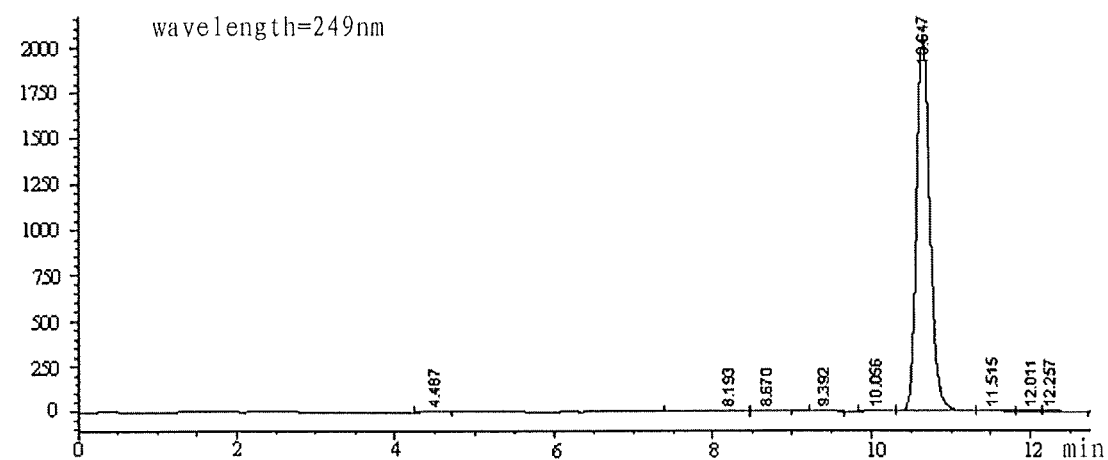
FIG. 3 is a HPLC chromatogram of epothilone A having the chromatographic purity of higher than 99.0% after the separation and purification.

The HPLC chromatograms of pure products of epothilone B and epothilone A obtained according to above methods are shown in FIGS. 2 and 3 respectively.

Example 6

Preparation of Amorphous Powders of Epothilone B and Epothilone A

Epothilone B and epothilone A with high purities obtained from Example 5 were dissolved in t-butanol respectively and lyophilized so as to obtain amorphous powders.

0.52 g epothilone B was dissolved in 50 ml t-butanol by heating, and then cooled to room temperature. The solution was then lyophilized at −20° C. for 48 hours in VIRTIS Genesis freeze-dryer. The lyophilized product was further dried at 30° C. for 96 hours under high vacuum, and then at 52° C. for 48 hours under high vacuum. Obtained lyophilized powder was measured by X-ray diffraction.

0.41 g epothilone A was dissolved in 30 ml t-butanol by heating, and then cooled to room temperature. The solution was then lyophilized at −20° C. for 48 hours in VIRTIS Genesis freeze-dryer. The lyophilized product was further dried at 30° C. for 96 hours under high vacuum, and then at 52° C. for 48 hours under high vacuum. Obtained lyophilized powder was measured by X-ray diffraction.

Figure 4:
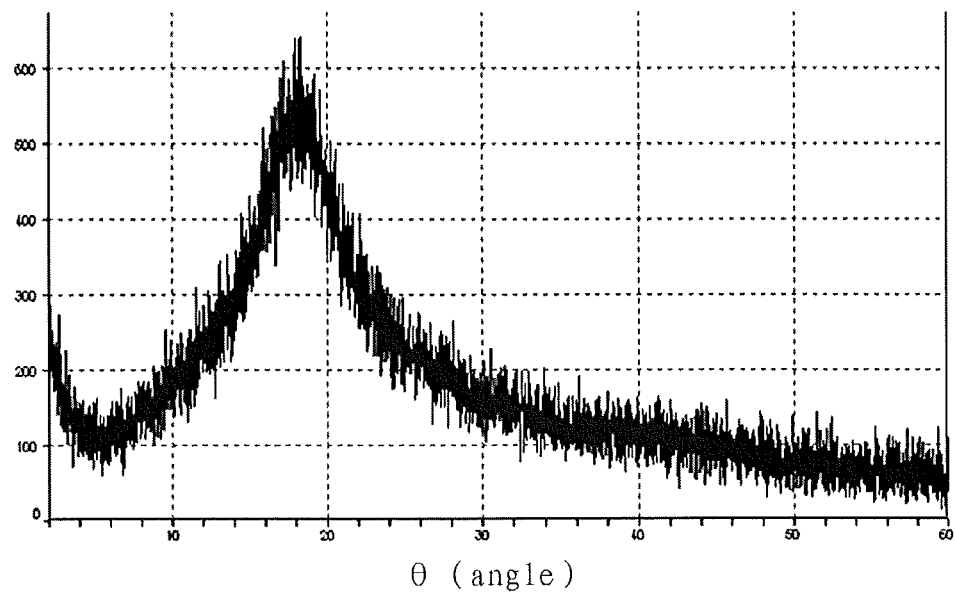
FIG. 4 is a PXRD graph of the amouphous powder of lyophilized epothilone B (2θ(degree), using Cukα, λ=0.154056 nm)
Figure 5:
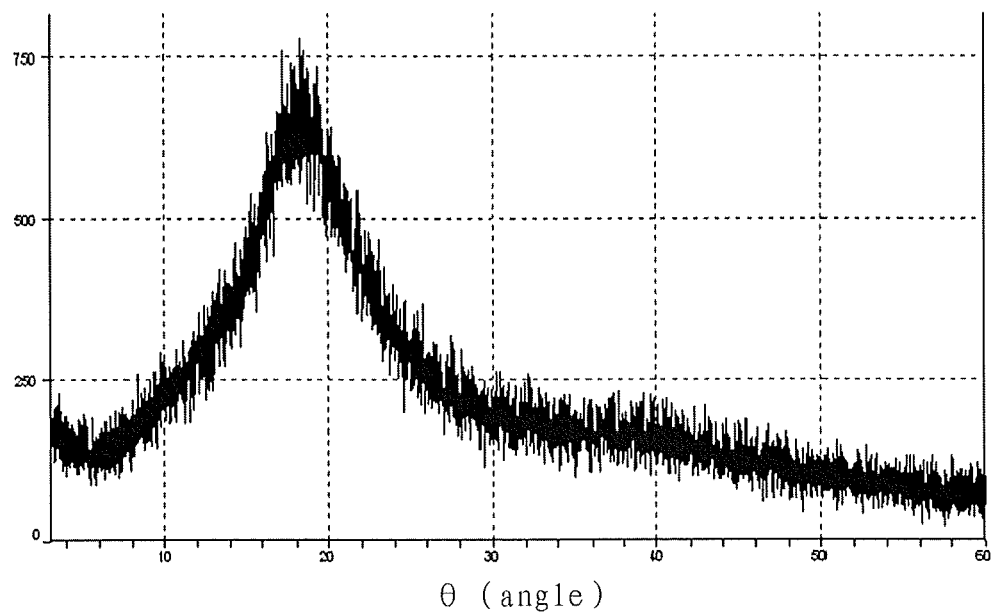
FIG. 5 is a PXRD graph of the amouphous powder of lyophilized epothilone A (2θ(degree), using Cukα, λ=0.154056 nm).

The PXRD graphs of epothilone B and epothilone A obtained according to above methods are shown in FIGS. 4 and 5 (The measurement of the powders by X-ray diffraction was performed on Rigaku D/max-2200).

Comparative Example 1

After dissolving 5 g crude crystal containing epothilones B and A obtained from Example 1 in 5 ml dichloromethane, the solution was loaded on a second normal phase silica gel column (4 cm*80 cm, 300 g silica gel). The silica gel column was balanced by petroleum ether/acetone with a ratio of 1:1, and then gradient eluted in sequence with petroleum ether/acetone with ratios of 90:10, 85:15, 83:17 and 80:20. Fractions were collected sectionally. Desired fractions containing epothilone B and desired fractions containing epothilone A were collected and combined respectively after analysis by HPLC, and then condensed respectively until dry. Finally, 0.94 g epothilone B of 98.3% (yield 35%) and 0.72 g epothilone A of 95.2% (yield 35%) were obtained.

Comparative Example 2

After dissolving 5 g crude crystal containing epothilones B and A obtained from Example 1 in 5 ml dichloromethane, the solution was loaded on a second normal phase silica gel column (4 cm*80 cm, 300 g silica gel). The silica gel column was balanced by petroleum ether/dichloromethane with a ratio of 1:1, and then gradient eluted in sequence with petroleum ether/acetone/trichloromethane with ratios of 90:10:10, 85:15:10, 83:17:10 and 80:20:10. Fractions were collected sectionally. Desired fractions containing epothilone B and desired fractions containing epothilone A were collected and combined respectively after analysis by HPLC, and then condensed respectively until dry. Finally, 0.97 g epothilone B of 98.4% (yield 36%) and 0.83 g epothilone A of 95.7% (yield 40%) were obtained.

Comparative Example 3

After dissolving 5 g crude crystal containing epothilones B and A obtained from Example 1 in 5 ml dichloromethane, the solution was mixed with silica gel, and the mixture was dried under vacuum. The dried mixture was loaded on a second normal phase silica gel column (4 cm*80 cm, 300 g silica gel). The silica gel column was filled by dry process and compacted by vacuuming, and then gradient eluted in sequence with petroleum ether/acetone/dichloromethane with ratios of 90:10:10, 85:15:10, 83:17:10 and 80:20:10. Fractions were collected sectionally. Desired fractions containing epothilone B and desired fractions containing epothilone A were collected and combined respectively after analysis by HPLC, and then condensed respectively until dry. Finally, 0.81 g epothilone B of 98.7% (yield 30%) and 0.70 g epothilone A of 95.4% (yield 34%) were obtained.

What is claimed is:

1. A method for separation and purification of epothilones B and A, characterized in that, the separation and purification of epothilones B and A are performed by a normal phase silica gel column chromatography; and the method comprises: dissolving a sample containing epothilones B and A in $C_1$-$C_7$ alkyl halide compound(s) to form a mixture, wherein the mixture is mixed with silica gel or not;
   loading the mixture on a silica gel column;
   gradient eluting the silica gel column with a normal phase silica gel column eluent;
   collecting fractions; and
   obtaining products;
   wherein the normal phase silica gel column eluent is chosen from a $C_1$-$C_7$ hydrocarbon, a $C_1$-$C_7$ alkyl halide compound, a $C_1$-$C_7$ ketone, $C_1$-$C_7$ ester, or any combination thereof, and wherein the $C_1$-$C_7$ hydrocarbon is chosen from petroleum ether, n-hexane, cyclohexane, n-heptane, or any combination thereof, the $C_1$-$C_7$ alkyl halide compound is chosen from dichloromethane, trichloromethane, bromoethane, or any combination thereof, the $C_1$-$C_7$ ketone is chosen from acetone, butanone, or any combination thereof, and the $C_1$-$C_7$ ester is chosen from ethyl acetate, isobutyl acetate, or any combination thereof; and
   wherein the normal phase silica gel column is balanced with $C_1$-$C_7$ alkyl halide compound(s) before use.

2. The method according to claim 1, wherein the method comprises:
   dissolving a sample containing epothilones B and A in $C_1$-$C_7$ alkyl halide compound(s) to form a mixture, wherein the mixture is mixed with silica gel of a first normal phase silica gel column or not;
   loading the mixture on the first normal phase silica gel column;
   gradient eluting the silica gel column with a normal phase silica gel column eluent;
   collecting fractions containing epothilone B and epothilone A;
   combining the fractions containing epothilone B and epothilone A;
   concentrating the combined fractions followed by crystallization to obtain a crude crystal containing epothilones B and A;
   dissolving the crude crystal containing epothilones B and A in $C_1$-$C_7$ alkyl halide compound(s) to form a second mixture, wherein the second mixture is mixed with silica gel of a second normal phase silica gel column or not;

loading the second mixture on a second normal phase silica gel column;

gradient eluting the silica gel column with a normal phase silica gel column eluent;

collecting fractions containing epothilone B and fractions containing epothilone A respectively;

concentrating fractions containing epothilone B and fractions containing epothilone A respectively and crystallizing fractions containing epothilone B.

3. The method according to claim 1, wherein the $C_1$-$C_7$ alkyl halide compound(s) is selected from one of dichloromethane, trichloromethane and a combination thereof.

4. The method according to claim 2, wherein the eluent of the first normal phase silica gel column is a combination of petroleum ether and acetone in a volume ratio of 3-9:1, or a combination of petroleum ether and ethyl acetate in a volume ratio of 1-9:1.

5. The method according to claim 4, wherein the eluent of the second normal phase silica gel column is a combination of acetone and petroleum ether in a volume ratio of 1:3-9, or a combination of petroleum ether and acetone in a volume ratio of 1:3-9 with either dichloromethane or trichloromethane and the volume of dichloromethane or trichloromethane is 5%-50% of the total volume.

6. The method according to claim 5, wherein the fractions containing epothilones B and/or A eluted from the silica gel columns are measured by HPLC.

7. The method according to claim 6, wherein a solvent used for crystallization is n-heptane, ethyl acetate or a combination thereof.

8. The method according to claim 7, wherein the solvent used for crystallization is a combination of n-heptane and ethyl acetate having a volume ratio of 1:1.

9. The method according to claim 8, wherein crystallization is performed by dissolving a crude product containing epothilones B and A, or a crude product containing epothiloine B in an appropriate amount of ethyl acetate, adding n-heptane therein, letting obtained solution stand at room temperature, then cooling to 4° C. to obtain crystals.

10. The method according to claim 1, wherein the sample containing epothilones B and A is a product separated from a fermentation broth of myxobacteria via non-polar macroporous polymeric adsorbents.

11. The method according to claim 10, wherein the sample containing epothilones B and A is prepared by a process comprising:

adding a resin of a first non-polar macroporous polymeric adsorbent column into the fermentation broth of myxobacteria, filtering by a vibrating screen and washing by water to remove impurities at the same time, then loading the resin in a column, gradient eluting with an alcohol solution, and combining fractions containing epothilones B and A;

diluting the combined fractions containing epothilones B and A to an appropriate concentration, then loading the diluted solution on a second non-polar macroporous polymeric adsorbent column, gradient eluting with an alcohol solution, collecting fractions containing epothilones B and A, combining the fractions containing epothilones B and A and then obtaining the sample containing epothilones B and A.

12. The method according to claim 11, wherein the first non-polar macroporous polymeric adsorbent is XAD-1600 type resin; and the second non-polar macroporous polymeric absorbent is H41 type resin.

13. The method according to claim 12, wherein an eluent used for the first non-polar macroporous polymeric adsorbent column is an ethanol solution of 30%400% by volume; and an eluent used for the second non-polar macroporous polymeric adsorbent column is an ethanol solution of 30%-80% by volume.

14. The method according to claim 13, wherein the fractions containing epothilone B and A eluted from the first and the second non-polar macroporous polymeric absorbent columns are measured by HPLC.

15. The method according to claim 14, wherein the separation and purification of epothilone B and epothilone A are performed by chromatography of the normal phase silica gel column, the method comprises:

(1) filtering the fermentation broth wherein XAD-1600 type resin is added by a vibrating screen and washing by water to remove impurities at the same time, then loading the resin in a column, gradient eluting with an ethanol solution of 30%-100% by volume, collecting fractions sectionally, collecting respectively fractions containing epothilone B and epothilone A after analysis by HPLC, and combining fractions containing epothilone B and epothilone A;

(2) diluting combined fractions containing epothilones B and A to form an alcohol solution with an appropriate concentration, or concentrating combined fractions to a suitable volume by vacuum evaporation and then diluting to form an alcohol solution with an appropriate concentration, loading the alcohol solution on H41 type resin column, gradient eluting with an alcohol solution of 30%-80% by volume, collecting fractions sectionally, collecting fractions containing epothilone B and epothilone A after analysis by HPLC, combining fractions containing epothilone B and epothilone A, concentrating the combined fractions by vacuum evaporation until dry to obtain a sample containing epothilones B and A;

(3) dissolving the sample containing epothilones B and A in trichloromethane or dichloromethane, wherein the mixture is mixed with silica gel of a first normal phase silica gel column or not;

loading the mixture on the first normal silica gel column, gradient eluting by a mixture of petroleum ether/acetone or a mixture of petroleum ether/ethyl acetate, collecting fractions sectionally, collecting fractions containing epothilone B and epothilone A after analysis by HPLC, combining fractions containing epothilone B and epothilone A, concentrating the combined fractions by vacuum evaporation until dry, performing crystallization by a mixed solvent of ethyl acetate/n-heptane to obtain crude crystal containing epothilones B and A;

(4) dissolving the crude crystal containing epothilones B and A in trichloromethane or dichloromethane, wherein the second mixture is mixed with silica gel of a second normal phase silica gel column or not;

loading the second mixture on the second normal silica gel column, gradient eluting by a mixture of petroleum ether/acetone or a mixture of petroleum ether/acetone/trichloromethane, collecting fractions sectionally, collecting respectively fractions containing epothilone B and fractions containing epothilone A after analysis by HPLC;

(5) performing crystallization on fractions containing epothilone B by ethyl acetate/n-heptane, dissolving the crystal containing epothilone B in t-butanol and lyophilizing the solution to obtain a product of epothilone B with a high purity in a form of amorphous power;

dissolving epothilone A in t-butanol and then lyophilizing to obtain a product of epothilone A with a high purity in a form of amorphous power.

16. A method for separation and purification of epothilones B and A, characterized in that, the separation and purification of epothilones B and A are performed by a normal phase silica gel column chromatography, and the method comprises:

dissolving a sample containing epothilones B and A in $C_1$-$C_7$ alkyl halide compound(s) to form a mixture, wherein the mixture is mixed with silica gel or not;

loading the mixture on a normal phase silica gel column;

gradient eluting the silica gel column with a normal phase silica gel column eluent;

collecting fractions; and obtaining products;

wherein the normal phase silica gel column is balanced with the $C_1$-$C_7$ alkyl halide compound(s) before use.

17. A method according to claim 1 wherein a mass ratio of the silica gel used in the first normal phase silica gel column to the sample is 5-10:1; and a mass ratio of the silica gel used in the second normal phase silica gel column to a crude crystal containing epothilones B and A is 50-200:1.

18. A method according to claim 16 wherein a mass ratio of the silica gel used in the first normal phase silica gel column to the sample is 5-10:1; and a mass ratio of the silica gel used in the second normal phase silica gel column to a crude crystal containing epothilones B and A is 50-200:1.

19. A method according to claim 16, wherein the normal phase silica gel column eluent is chosen from a $C_1$-$C_7$ hydrocarbon, a $C_1$-$C_7$ alkyl halide compound, a $C_1$-$C_7$ ketone, a $C_1$-$C_7$ ester, or any combination thereof, and wherein the $C_1$-$C_7$ hydrocarbon is chosen from petroleum ether, n-hexane, cyclohexane, n-heptane, or any combination thereof, the $C_1$-$C_7$ alkyl halide compound is chosen from dichloromethane, trichloromethane, bromoethane, or any combination thereof, the $C_1$-$C_7$ ketone is chosen from acetone, butanone, or any combination thereof, and the $C_1$-$C_7$ ester is chosen from ethyl acetate, isobutyl acetate, or any combination thereof.

20. The method according to claim 19, wherein the normal phase silica gel column eluent is chosen from petroleum ether, ethyl acetate, acetone, trichloromethane, dichloromethane, or any combination thereof.

21. The method according to claim 1, wherein the normal phase silica gel column eluent is chosen from petroleum ether, ethyl acetate, acetone, trichloromethane, dichloromethane, or any combination thereof.

* * * * *

UNITED STATES PATENT AND TRADEMARK OFFICE
CERTIFICATE OF CORRECTION

PATENT NO. : 8,906,947 B2  
APPLICATION NO. : 12/865581  
DATED : December 9, 2014  
INVENTOR(S) : Wang et al.

It is certified that error appears in the above-identified patent and that said Letters Patent is hereby corrected as shown below:

In the Claims:
Column 12, Claim 13, Line 3: Correct "of30%400% by volume;"
　　　　　　　　　　　to read -- of 30% - 100% by volume; --

Signed and Sealed this
Twenty-first Day of April, 2015

Michelle K. Lee
*Director of the United States Patent and Trademark Office*